United States Patent [19]
Stotts et al.

[11] Patent Number: 5,782,884
[45] Date of Patent: Jul. 21, 1998

[54] RATE RESPONSIVE CARDIAC PACEMAKER WITH PEAK IMPEDANCE DETECTION FOR RATE CONTROL

[75] Inventors: Lawrence J. Stotts; Edward A. Schroeppel, both of Lake Jackson, Tex.

[73] Assignee: Sulzer Intermedics Inc., Angleton, Tex.

[21] Appl. No.: 743,299

[22] Filed: Nov. 5, 1996

[51] Int. Cl.[6] ............................................. A61N 1/365
[52] U.S. Cl. ............................................. 607/17
[58] Field of Search ............................. 607/9, 17–19, 607/24, 28

[56] References Cited

U.S. PATENT DOCUMENTS

| | | |
|---|---|---|
| 4,140,132 | 2/1979 | Dahl . |
| 4,535,774 | 8/1985 | Olson . |
| 4,686,987 | 8/1987 | Salo et al. . |
| 4,688,573 | 8/1987 | Alt . |
| 4,719,921 | 1/1988 | Chirife . |
| 4,730,619 | 3/1988 | Konig et al. . |
| 4,733,667 | 3/1988 | Olive et al. . |
| 4,773,401 | 9/1988 | Citak et al. . |
| 4,865,036 | 9/1989 | Chirife . |
| 4,926,863 | 5/1990 | Alt . |
| 5,002,052 | 3/1991 | Haluska . |
| 5,154,171 | 10/1992 | Chirife . |
| 5,168,869 | 12/1992 | Chirife . |
| 5,174,286 | 12/1992 | Chirife . |
| 5,190,035 | 3/1993 | Salo et al. . |
| 5,197,467 | 3/1993 | Steinhaus et al. . |
| 5,201,808 | 4/1993 | Steinhaus et al. . |
| 5,235,976 | 8/1993 | Spinelli ......................... 607/25 |
| 5,309,917 | 5/1994 | Wang et al. ................... 128/696 |
| 5,334,222 | 8/1994 | Salo et al. ..................... 607/24 |
| 5,417,715 | 5/1995 | Noren et al. ................... 607/9 |
| 5,417,717 | 5/1995 | Salo et al. ..................... 607/24 |
| 5,500,005 | 3/1996 | Strandberg et al. .......... 607/17 |
| 5,507,785 | 4/1996 | Deno ............................. 607/24 |
| 5,531,772 | 7/1996 | Prutchi ......................... 607/17 |

*Primary Examiner*—Jeffrey R. Jastrzab
*Attorney, Agent, or Firm*—John R. Merkling

[57] ABSTRACT

An implantable, rate responsive pacemaker, sensitive to impedance changes in the heart, wherein the cardiac pacing rate and maximum cardiac pacing rate, or either of them, are adjusted as a function of an interval between either the administration of a pacing pulse or the detection of the R-wave and the occurrence of a maximum detected impedance, called the intercept interval. Because an intercept point in derivative of the impedance curve is detected, the apparatus and method are insensitive to electrode characteristics, electrode movement, body posture or other factors which could affect the magnitude of the detected impedance. The information contained in the intercept interval can also be combined with other sensed or calculated information to set the desired rates.

16 Claims, 4 Drawing Sheets

RATE RESPONSIVE CARDIAC PACEMAKER WITH PEAK IMPEDANCE DETECTION FOR RATE CONTROL

FIELD OF OUR INVENTION

Our invention relates to rate responsive cardiac pacemakers, and more particularly to cardiac pacemakers which automatically adjust their pacing parameters, for example the pacing rate, in response to measured impedance, and most particularly in response to measured impedance changes in the heart.

BACKGROUND OF OUR INVENTION

Implanted cardiac pacemakers are employed to assist patients suffering from severe bradycardia or chronotropic incompetence. Originally, such pacemakers restored a normal, at rest, heart rate by providing a fixed rate or narrow range of externally programmable rates. However, these pacemakers failed to meet patients' metabolic demands during exercise. Consequently, socalled "rate adaptive" or "rate responsive" pacemakers were developed. These pacemakers sense some parameter correlated to physiologic need and adjust the pacing rate of the pacemaker.

Numerous parameters have been selected to attempt to correlate pacing rate to the actual physiologic need of the patient. Blood pH, blood temperature, QT interval, vibration, respiration rate, or accelerations due to physical activity have been employed with varying degrees of success. Among these parameters are the stroke volume of the heart and the minute volume of respiration, both parameters being inferred from impedance measurements. The stroke volume of the heart is defined as the volume of blood expelled by the ventricle in a single beat. It is equal to the difference between the end diastolic volume and the end systolic volume. In normal human subjects with healthy hearts, the stroke volume of the heart has been found to remain relatively constant over a wide range of exertion. Increases in cardiac output required to meet physiologic needs are primarily provided by increased heart rate. For certain patients with pacemakers whose heart rate is controlled by the pacemaker, increased cardiac output during exertion is provided by the heart attempting to increase its stroke volume. The stroke volume cannot increase, however, by a factor more than about two or two and a half times. Increasing the pacing rate is therefore still desired. It has been proposed to utilize the body's tendency to attempt to increase stroke volume to adjust the pacing rate of an implanted pacemaker, thereby providing an appropriate physiologic pacing rate.

For example, in Salo et al., U.S. Pat. No. 4,686,987 a stroke volume responsive, rate adjusting pacemaker is described. An AC signal is inserted through an implanted lead. The changing volume of the heart alters the impedance between the lead electrode and another electrode or the can of the pacemaker, and the changing impedance modulates the detected AC signal. By isolating the resulting amplitude envelope, an indication of the changing impedance can be obtained. This fluctuation is deemed to be a function, at least in part, of the action of the heart.

Chirife, U.S. Pat. No 5,154,171, proposed that metabolic demands should be related to the ejection fraction, as a more accurate measure of true physiologic need. The ejection fraction is the stroke volume divided by the end diastolic volume. The stroke volume is taken to be the end diastolic volume minus the end systolic volume. The observed impedance of the heart is deemed to be a function of volume of the heart and therefore to be an indication of the desired measurements when taken at an appropriate time.

In practice, intracardiac impedance measurements reflect electrical conductivity in other parts of the body and are not solely related to the beating of the heart. Other motions and factors also change the impedance characteristics. One example is change due to respiration. It has been proposed that the minute volume of respiration could be detected by an appropriate impedance measurement. See, for example, U.S. Pat. No 4,901,725 entitled "Minute Volume Rate Responsive Pacemaker" to Nappholz et al.

U.S. Pat. No. 5,201,808 to Steinhaus et al., describes several attempts to detect the minute volume due to respiration in an accurate manner. Steinhaus et al. also proposes a relatively high frequency waveform as the appropriate means for measuring the spatial impedance as a function of the patient's pleural pressure. Steinhaus et al. notes that different frequencies for the testing pulse are adapted to detecting different phenomenan. That is, one range of frequency may be more appropriate for detecting changes due to heart beats, another would be more appropriate for detecting minute volume.

U.S. Pat. No. 5,197,467 to Steinhaus, et al. describes charging a capacitor (see particularly FIG. 2) and discharging the capacitor through the heart or a portion of the body for a selected brief interval. The voltage remaining on the capacitor after the period of discharge can be detected through a buffer, converted to digital information, and used to estimate the impedance of that portion of the patient's body between the cathode and anode electrodes.

However, a problem raised by the use of impedance as an indirect measure of physiologic need is the indeterminate current path. The impedance of the body is generally measured between at least two points within the body, perhaps an electrode in the heart and a second electrode or the can of an implanted device. The path between these two points, however, is inherently indeterminate. Moreover, the measurement may be affected by motion of the electrode tip, by conditions surrounding the tip or by electrical capacitances of adjacent electrodes (as described in Steinhaus et al. '808), or other factors. Myopotentials, pacing artifacts, pacing afterpotentials, and general electrical noise can all mask the desired measurement. It is desirable, therefore, to eliminate or minimize the effect of background interference or apparent baseline impedance so that changes in impedance due to the relatively fast beating heart or to respiration may be amplified and more easily detected.

One approach to solving the problem of electrical noise has been proposed by Prutchi in commonly assigned U.S. Pat. No. 5,531,772, incorporated herein by reference. Prutchi discloses a cardiac pacemaker which senses varying impedance of the heart by discharging an active capacitor through an electrode implanted within the heart to a second electrode or to the case or can of the pacemaker. The active capacitor is discharged for a selected short period of time after which the voltage remaining on the capacitor is buffered for further processing. Prior to discharge of this active capacitor, however, the cardiac pacemaker samples the electrical condition of the heart or the body of the patient between the two electrodes by charging a passive capacitor. The voltage on this passive capacitor is also buffered and held in a sample and hold circuit until the active capacitor has been discharged. The voltage on the passive capacitor is subtracted from the residual voltage on the active capacitor and the resulting voltage is held in a sample and hold circuit. The voltage held in the sample and hold circuit is communicated to a microprocessor for adjustment of the rate of the pacemaker.

Another approach has been suggested by Deno in commonly assigned U.S. Pat. No. 5,507,785, incorporated herein by reference, wherein common interfering signals such as the intracardiac electrogram, myoelectric signals, pacing artifacts and other pacing after-potentials are reduced or eliminated from the measurement of the impedance by the use of a biphasic test signal and measurement process. The cardiac pacemaker has a signal injector which produces biphasic test pulses of very brief duration, for example, between two and fifty microseconds. The pulses are preferably of similar duration and magnitude, though of opposite polarity. They are delivered by the signal injector across a selected set of electrodes. The pulses are preferably of substantially constant current. The basic structure of the Deno apparatus is described herein in connection with our invention, but it will be understood that other apparatus and methods for detecting change in impedance, such as those described in the patents hereinabove mentioned, could also be used.

SUMMARY OF OUR INVENTION

We have invented an implantable, rate responsive pacemaker, sensitive to impedance changes in the heart, wherein the cardiac pacing rate and maximum cardiac pacing rate, or either of them, are adjusted as a function of an interval between either the administration of a pacing pulse or the detection of the R-wave and the occurrence of a maximum detected impedance, which we will call the intercept interval. Because a maximum in the impedance curve can be detected using the zero intercept of the derivative or the impedance curve, the apparatus and method are insensitive to electrode characteristics, electrode movement, body posture or other factors which could affect the magnitude of the detected impedance. The information contained in the intercept interval can also be combined with other sensed or calculated information to set the desired rates. For example, motion of the body may be detected with an accelerometer (see, e.g., Alt U.S. Pat. No. 4,926,863), or the time of day may be used to simulate a circadian rhythm (see, e.g., Adkins, et al. U.S. Pat. No. 4,922,930).

It is the principal object of our invention, therefore, to provide a rate-responsive pacemaker which can more accurately respond to impedance changes in the heart.

A further object of our invention is to provide an apparatus and method for use with an impedance sensitive pacemaker which can reject background and interference signals such as the intracardiac electrogram, myoelectric signals, pacing potential artifacts, and pacing after-potentials, for example.

These and other objects and features of our invention will be apparent to the skilled artisan from the following detailed description taken with reference to the accompanying drawings.

DETAILED DESCRIPTION OF OUR PREFERRED EMBODIMENT

Figure 1:
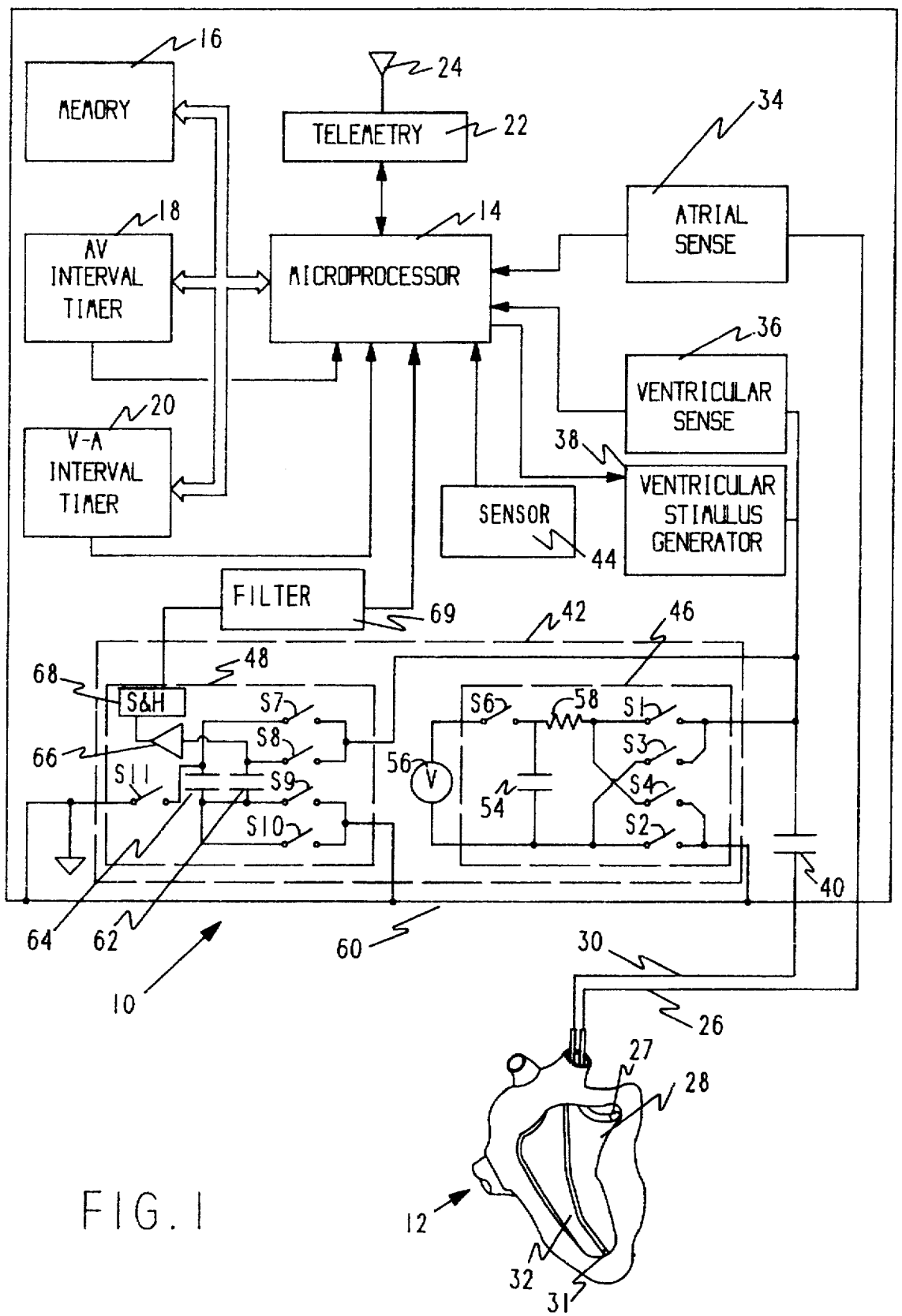
FIG. 1 is a block diagram of a first preferred embodiment of a rate adaptive pacemaker according to our invention.

We will now describe the preferred embodiment of our invention with reference to the accompanying figures. Like numerals will be used to designate like parts throughout. Referring now to FIG. 1, a pacemaker, generally designated 10, is illustrated in schematic fashion with connection to a human heart 12. For ease of illustration, we have elected to describe our invention in connection with a pacemaker having atrial sensing and ventricular sensing and pacing. It should be understood, however, that our invention can be employed for sensing in the atrium, the ventricle or both and that both atrial or ventricular pacing or either of them could be provided without departing from the teachings of our invention. In addition, the features of our invention could also be combined with an implantable defibrillator/cardioverter.

With this understanding, the illustrated pacemaker 10 comprises a microprocessor 14 which executes various control programs to regulate the action of the pacemaker. The microprocessor 14 is connected to additional memory 16 for the storage of programs and data as may be needed. As is known in the art, one or more internal clocks may be provided to permit timing of various events. For example, an A-V interval timer 18 may be provided. Similarly, a V-A interval timer 20 may also be provided, as known in the art. The microprocessor is provided with a telemetry circuit 22 so that communication can be had across an antenna 24 to an external programmer (not shown). Telemetry permits an attending physician to obtain data and information from the pacemaker and to control the pacemaker to set various selectable parameters, as known in the art.

The pacemaker 10 is connected to the heart 12 through a first lead 26 to an electrode 27 in the atrium 28 and through a second lead 30 to an electrode 31 in the ventricle 32. An indifferent electrode is provided to complete the electrical circuit through the body. In the illustrated embodiment, a can 60 or outer casing of the pacemaker serves as the indifferent electrode. Bipolar leads can also be used with our invention as well as the unipolar leads illustrated here. Atrial sensing, through an atrial sense circuit 34, and ventricular sensing, through a ventricular sense circuit 36, provide information to the microprocessor concerning the condition and responsiveness of the heart. In addition, pacing pulses are provided to the ventricle from a ventricular stimulus generator 38. It is clearly within the scope of those skilled in the art to provide atrial pacing, should that be desired, or to provide cardioversion/defibrillation capabilities in response to the detected condition of the heart. Stimulation of the heart is passed through a coupling capacitor 40 in a conventional fashion.

To control the pulse rate of the ventricular stimulus generator 38, the microprocessor acquires information on the condition of the heart through an impedance circuit 42. The impedance circuit 42 detects changes in impedance primarily due to the changing shape of the heart, which is related to the physical shape of the heart as it beats and pumps blood. This information can be used to derive a measure of the stroke volume or ejection fraction or end diastolic volume of the heart. Furthermore, the shape of the impedance waveform can provide information on other cardiac timing parameters such as isovolumetric contraction time, pre-ejection period, and so on.

In addition to the measurement of impedance, a sensor 44 may also be provided to obtain an indication of physiologic need and adjust the pacing rate. Such a sensor may be an accelerometer, as described by Dahl, U.S. Pat. No. 4,140,132, (incorporated herein by reference), a temperature sensor, as described by Alt, U.S. Pat. No. 4,688,573 (also incorporated herein by reference), or any other suitable sensor of a parameter which may be correlated to physiologic need of the patient.

Figure 2:
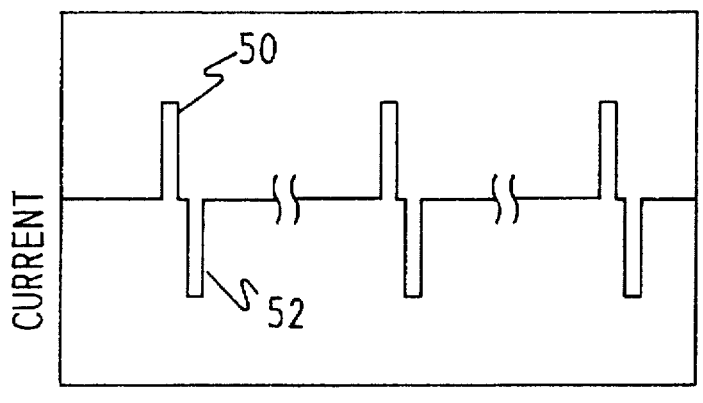
FIG. 2 is a graph of a series of biphasic pulses.

The impedance circuit 42 comprises a biphasic signal injector 46 and a signal detector 48. The biphasic signal injector 46 produces short, essentially symmetrical biphasic constant current pulses to detect the varying impedance of the heart. Each pulse has a duration on the order of one (1) to fifty (50) microseconds and an amplitude of 0.1 to 2 mA. The resulting detected voltage across the heart valve will be on the order of 50 to 1000 mV. As shown in FIG. 2, the two pulses forming a pulse pair are substantially similar in duration and amplitude, polarity being reversed. Preferably, differences in magnitude and duration between a first pulse 50 and a second pulse 52 are no more than plus or minus ten percent. Most preferably, pulse amplitude is very similar, on the order of less than 0.1% variation. Greater variability in duration is acceptable. The symmetrical nature of the pulses permits the impedance effect associated with each pulse to be additively combined as will be explained hereafter, thus doubling the apparent magnitude of impedance change, while eliminating other effects.

The signal injector 46 has a storage capacitor 54 which is connected to a voltage source 56 through a switch S6. The voltage source 56 is preferably a battery or other power source conventionally used to provide electrical power within an implantable pacemaker. The switch S6, and all of the other switches described herein, are preferably controlled by the microprocessor 14. S6 is closed to connect the capacitor 54 to the voltage source 56, charging the capacitor. A large resistor 58 is connected between the capacitor 54 and the switches. The resistor 58 is large enough to be the dominant impedance in the circuit, effectively creating a constant current source. Consequently, since the voltage on capacitor 54 would be known, and the effective impedance would be well approximated by the impedance of the resistor 58, the current flowing through the switches S1, S2, S3, S4 into and through the heart would be known. By measuring the voltage drop across the heart, as more particularly described hereafter, the impedance can therefore be easily computed. When a biphasic pulse pair is produced, the switch S6 is opened and four switches S1, S2, S3, and S4, are closed and opened under the control of the microprocessor 14.

To produce the first pulse 50, switches S1 and S2 are closed while S3 and S4 remain open. This connects a first side of the capacitor 54 and resistor 58 through switch S1 to the lead 30 and electrode 31, and simultaneously connects a second side of the capacitor 54 through switch S2 to the indifferent electrode 60. The capacitor 54 and resistor 58 are relatively large over the duration of the pulse 50, so that the capacitor 54 and resistor 58 are essentially a constant current source. After a selected duration, for example five microseconds, switches S1 and S2 are opened by the microprocessor 14 and switches S3 and S4 are closed. This connects a first side of capacitor 54 and the resistor 58 through switch S4 to the indifferent electrode 60 and the second side of the capacitor 54 through switch S3 to the lead 30 and electrode 31, reversing the polarity of the current pulse being applied.

Preferably each pulse lasts between one and fifty microseconds and has a current magnitude on the order of between 0.1 and 2 mA, preferably 0.5 mA. Pulse pairs are produced on the order of one hundred times per second but may be produced from two times per second to several hundred times per second. Their duration, therefore, is about one thousand times shorter than the charging period during which switch S6 is connected to the capacitor 54. Consequently, because of the relatively large size of the capacitor 54 and its comparatively long charging period compared to the amplitude and duration of the pulses, the electrical condition of the capacitor 54 is essentially constant. Use of a balanced biphasic current pulse has the advantage that no net charge is transferred across the electrodes. This reduces electrode deposition and corrosion for greater biocompatibility.

The constant current source represented by the combination of the battery 56, the switch S6, the capacitor 54 and the resistor 58, could be implemented in other forms without departing from the teachings of our invention. For example, a solid state implementation could easily be employed by those skilled in the art such as a Wilson current mirror transistor circuit. See, for example, *The Art of Electronics*, 2nd ed. Paul Horowitz and Winfield Hill, Cambridge Univ. Press, 1989 pgs. 88–90.

Figure 6:
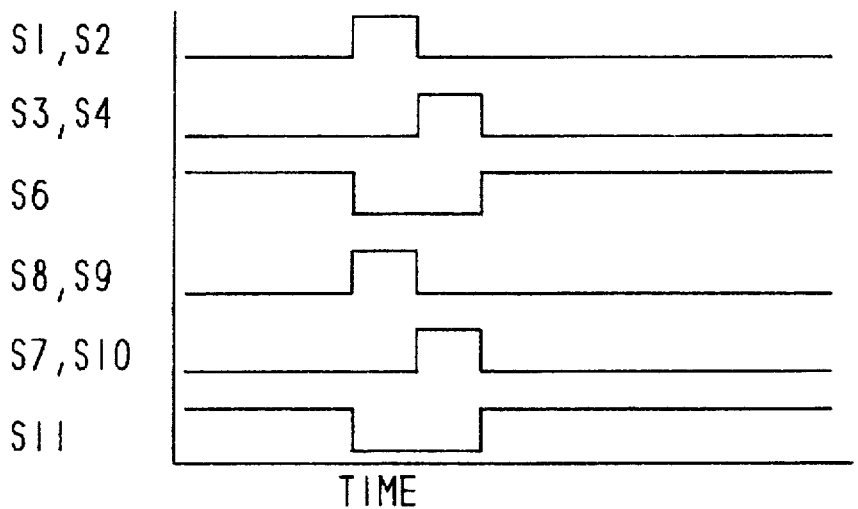
FIG. 6 is a timing diagram.

The voltages associated with the pulses of the biphasic pulse pair are detected through the detector 48. The detector 48 has two capacitors 62, 64 which are connected through four switches S7, S8, S9 and S10 to the electrode 31 and the indifferent electrode 60. During the first pulse 50, when switches S1 and S2 of the injector 46 are closed, switches S8 and S9 of the detector 48 are closed, as illustrated in timing diagram FIG. 6. This connects a first side of the first capacitor 62 through switch S8 to the lead 30 and electrode 31. A second side of the first capacitor 62 is connected through switch S9 to the indifferent electrode 60. When the first pulse 50 is over, and switches S1 and S2 are opened, switches S8 and S9 are also opened, as also shown in FIG. 6. The duration of the sampling occupies most or all of the injected current pulses, but preferably the duration $T_D$ and the size $C_s$ of the sampling capacitors 62, 64 are chosen so that $4 \times (Z_{LEAD} \times C_S) = T_D$. Thus, three to four time constants are available for sampling. As a result, the sampling capacitor voltages are less sensitive to capacitive loading or timing uncertainties. During the second pulse 52, when switches S3 and S4 are closed, switches S7 and S10 are also closed, connecting the second capacitor 64 to the electrodes. Switch S7 connects a first side of the second capacitor 64 to the lead 30 and electrode 31. Switch S10 connects a second side of the second capacitor 64 to the indifferent electrode 60. When the second pulse 52 ends and switches S3 and S4 are opened, switches S8 and S9 are also opened and a switch S11 is closed, connecting the first side of the second capacitor 64 to system ground. The second sides of both the first and second capacitor are connected together. This effectively "subtracts" the two charges from each other. Background effects, such as the intrinsic electrical condition of the heart, being common to both first capacitor 62 and second capacitor 64, would be eliminated by this subtractive combination. The desired voltage to be measured, resulting from the changing impedance of the heart, would be of opposite polarity because of the application of the biphasic current pulse. Consequently, the voltage across the series combination of the first capacitor 62 and the second capacitor 64 would be twice the voltage drop associated with a particular level of current injected through the heart. To make the desired measurement, the first side of the first capacitor 62 is connected to a buffer 66 which presents a high impedance. The output of the buffer 66 communicates with a sample-and-hold circuit 68 which samples the combined voltages of the first and second capacitor 62, 64. Alternatively, the first and second capacitors 62, 64 themselves can act as a sample-and-hold circuit. The value of this voltage is communicated from the sample-and-hold circuit 68 to the microprocessor 14 which uses the information to calculate the impedance of the heart 12. A low-pass filter 69 may be provided to smooth the information delivered to the microprocessor so that only an actual maximum impedance will be identified, as explained hereafter. The microprocessor could also be programmed to ignore local maxima associated with noise and other phenomenon.

Figure 3:
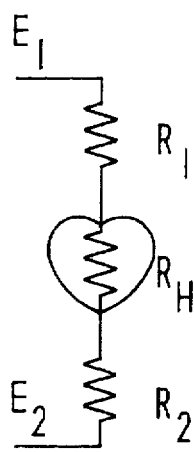
FIG. 3 is a schematic representation of a configuration of electrodes for measuring cardiac impedance.
Figure 4:
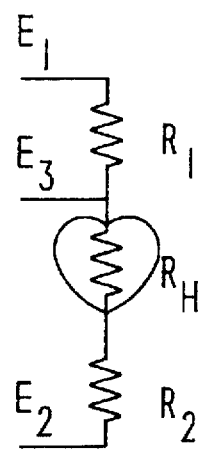
FIG. 4 is a schematic representation of a second configuration of electrodes for measuring cardiac impedance.
Figure 5:
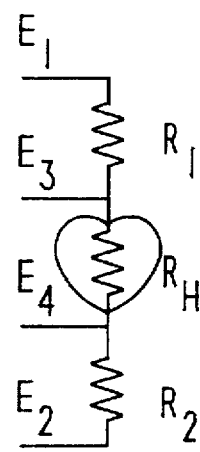
FIG. 5 is a schematic representation of a third configuration of electrodes for measuring cardiac impedance.

In FIG. 1, we have illustrated the biphasic signal injector 46 and the signal detector 48 using the same electrodes 31,60. This configuration is illustrated diagrammatically in FIG.3. FIG. 3 illustrates a first electrode E1 connected to a second electrode E2 through three lumped impedances or resistances R1, RH and R2. The resistances R1 and R2 may be associated with effects such as resistance in the leads themselves, resistance in other parts of the body or the effect of the interface between the electrode and the body. The impedance or resistance RH represents the impedance of the heart but other impedances, such as ventilation could also be selected. Although the desired changing impedance RH may be effectively measured using the configuration of FIG. 3, it is also possible to attempt to eliminate the effects of the other resistances R1 and R2 by utilizing additional electrodes. This is possible because the injector 46 and detector 48 are separate and distinct. For example, switches S7 and S8 of the detector 48 could be connected, not to the ventricular lead 30 and ventricular electrode 31, but to the atrial lead 26 and atrial electrode 27. This situation is represented diagrammatically in FIG. 4. In FIG. 4, three electrodes E1, E2 and E3 are illustrated. Additional resistance associated with electrode E3 and other electrodes mentioned hereafter are not illustrated. The detector 48 and injector 46 share a common electrode, for example electrode E2. This would represent a three electrode configuration. In addition, the injector 46 and the detector 48 may share no common electrodes. For example, the injector 46 could be connected through a bipolar electrode into the ventricle and the detector could be connected through a bipolar lead into the atrium. This configuration is illustrated diagrammatically in FIG. 5. The injector 46 might utilize electrodes E1 and E2, while the detector 48 would utilize electrode E3 and a fourth electrode E4. Additional electrode configurations could easily be selected to obtain the most favorable response or measurement of the changing impedance of the heart. Any of the electrodes E1, E2, E3 or E4 could be subdivided to connect to multiple locations within the patient's body.

Figure 7:
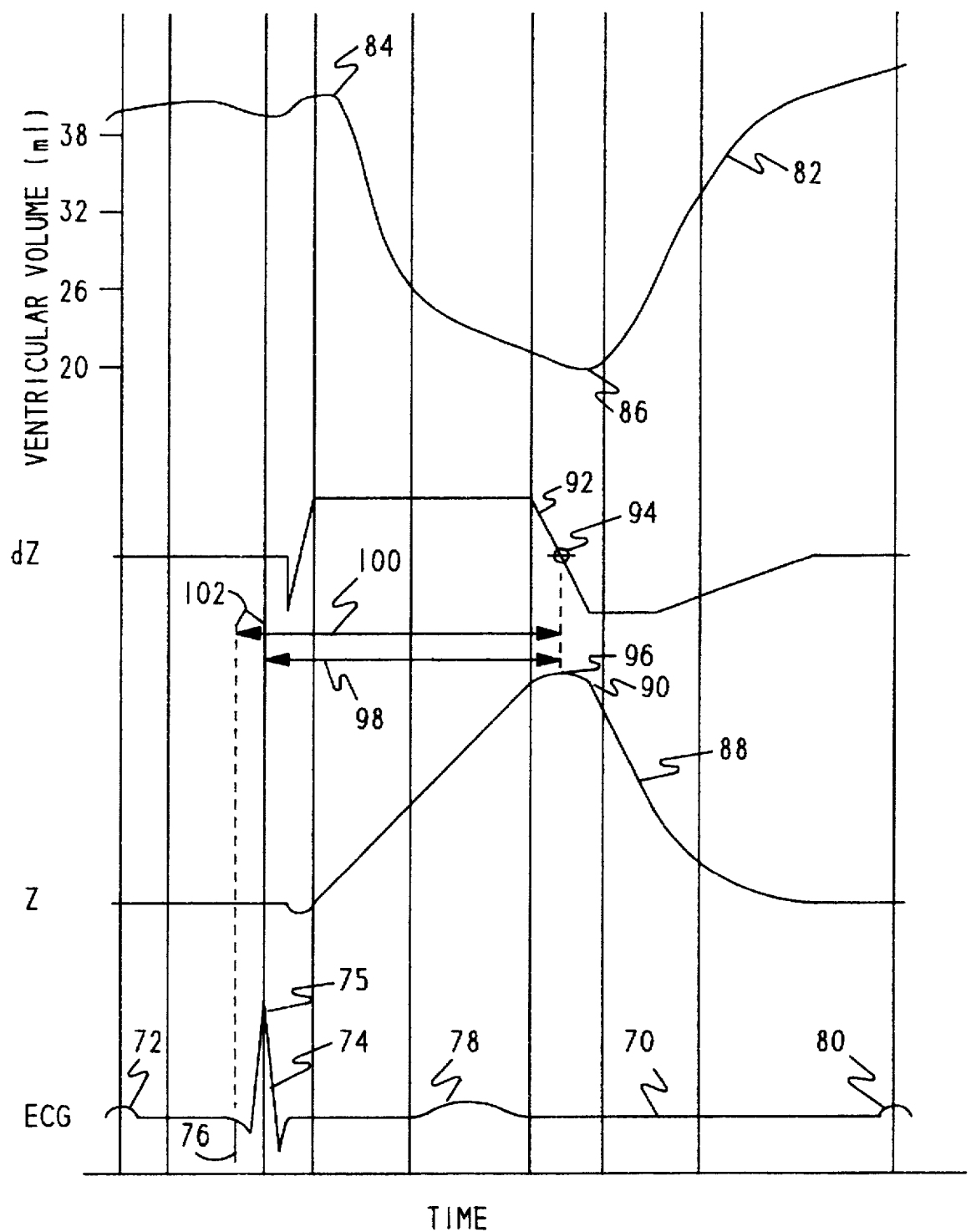
FIG. 7 is a graph of a cardiac electrogram, impedance, derivative of impedance and ventricular volume on a common time scale.

FIG. 7 illustrates the application of the acquired impedance data as utilized in our invention. In FIG. 7, two physiologic signals and two impedance related signals are displayed on the same time scale. An ECG signal 70, such as might be sensed by an implanted cardiac stimulator or pacemaker, is illustrated for a single cardiac cycle. The P wave 72 is illustrated as commencing the cycle. There follows the well known QRS complex 74. The most prominent feature of this complex 74 is the R wave 75. This electrical signal, indicative of the beginning of the contraction of the heart, may occur naturally in response to the heart's intrinsic pacemaker, or may be induced by a pacing pulse 76. The pacing pulse 76 is not shown to scale as it in general would have a substantially larger voltage magnitude than even the R-wave 75. After the QRS complex 74 is a T-wave 78, resetting the heart in preparation for another contraction. There follows another P-wave 80, and the cycle repeats itself. Associated with this electrical pattern in the heart, there is a corresponding mechanical reaction which provides the pumping action of the heart. This is illustrated by a graph of ventricular volume 82. Initially during the cardiac cycle, the heart is relatively relaxed and at its largest volume. With the commencement of the QRS complex 74, the heart begins a contraction at 84. This contraction continues to a minimum volume 86, usually at or slightly after the occurrence of the T-wave 78. This contraction expels the blood in the chambers of the heart into the body. The heart then relaxes and refills with blood, preparatory to the commencement of another cardiac cycle.

Impedance sensing as heretofore described can sense the changing impedance associated with the contraction of the heart. A simplified impedance waveform 88 is illustrated in FIG. 7. An unfiltered waveform would be expected to be much rougher, but the low-pass filter would smooth the waveform. As shown in FIG. 7, the impedance begins to increase as the heart begins to contract in response to the QRS complex, rising to a maximum 90 associated with the maximum contraction, or minimum volume 86 of the heart. The time derivative of the impedance waveform 88 is a derivative signal 92, also illustrated in FIG. 7. The derivative signal 92 can be expected to have a zero crossing or intercept 94 associated with a maximum point 96 of the impedance waveform 88, that is, with the maximum detected impedance. The zero crossing 94 would not be subject to an offset, or varying base impedance, as might otherwise be associated with the pure impedance signal. It is, consequently, relatively easy to detect precisely. Similarly, the occurrence of the pacing pulse 76 or the R-wave 75 are also relatively precisely detectable. The time of the pacing pulse 76 is unambiguously available to an implantable pacemaker. The R-wave 75 can be detected as a prominent feature of the ECG if occurring naturally, so that no artifacts from a preceding pacing pulse 76 interfere with detection. In FIG. 7, the QRS complex 74 is illustrated as a response to the applied pacing pulse 76. Naturally occurring QRS complexes, which would inhibit the application of a pacing pulse in modern pacemakers, could be expected to occur earlier than the expected application of a pacing pulse. The difference between the detected R-wave or the applied pacing pulse should be compensated as explained hereafter.

It is possible to measure the interval between the R-wave 75 and the intercept or zero crossing 94 representative of maximum impedance, an interval we will call the R-Z interval 98. Where a pacing pulse initiates the contraction of the heart, it is possible to measure an interval 100 from the pacing pulse to the intercept point or zero crossing 94. An approximate time period ΔT 102 can then be subtracted to approximate the location of the induced R-wave so that comparison can be made between R-Z intervals on the same basis.

It is known that the R-Z interval varies in response to different changes in the body. In particular, however, the R-Z interval varies in response to exercise, and metabolic demand and can, consequently, be used in the control of a pacemaker. A shortened R-Z interval may be indicative of increased exercise. On the other hand, rate changes in the heart lead to a change in the R-Z interval when such rate changes cause a change in cardiac output. An increase in cardiac output leads to an increase in the interval, whereas a drop in cardiac output shortens it. In general, the interval reacts to a change in cardiac output with a time constant of about 15 seconds. Thus, a rate responsive pacemaker, responding to the sensor 44 may increase a heart rate. At the same time, a detected shortening of the R-Z interval can indicate that the hemodynamic demand is not being met by the increased rate alone and require an additional incremental increase of rate to meet cardiac demand.

In addition, chronic prolongation of a R-Z interval may be indicative of the onset of life-threatening arrhythmias in certain clinical situations. A prolonged interval can be indicative of heart disease, and reflects an inhomogeneity in ventricular activation-recovery properties, a condition under which reentry and related arrhythmias may occur. Detected chronic R-Z interval elongation, therefore, can be utilized to select more aggressive therapies in an implanted cardioverter defibrillator, for example, the therapies described in Haluska et al. U.S. Pat. No. 5,002,052. Detection of chronic prolongation of the R-Z interval can cause a more aggressive therapy to be selected as an appropriate starting therapy in a so-called tiered therapy device.

Figure 8:
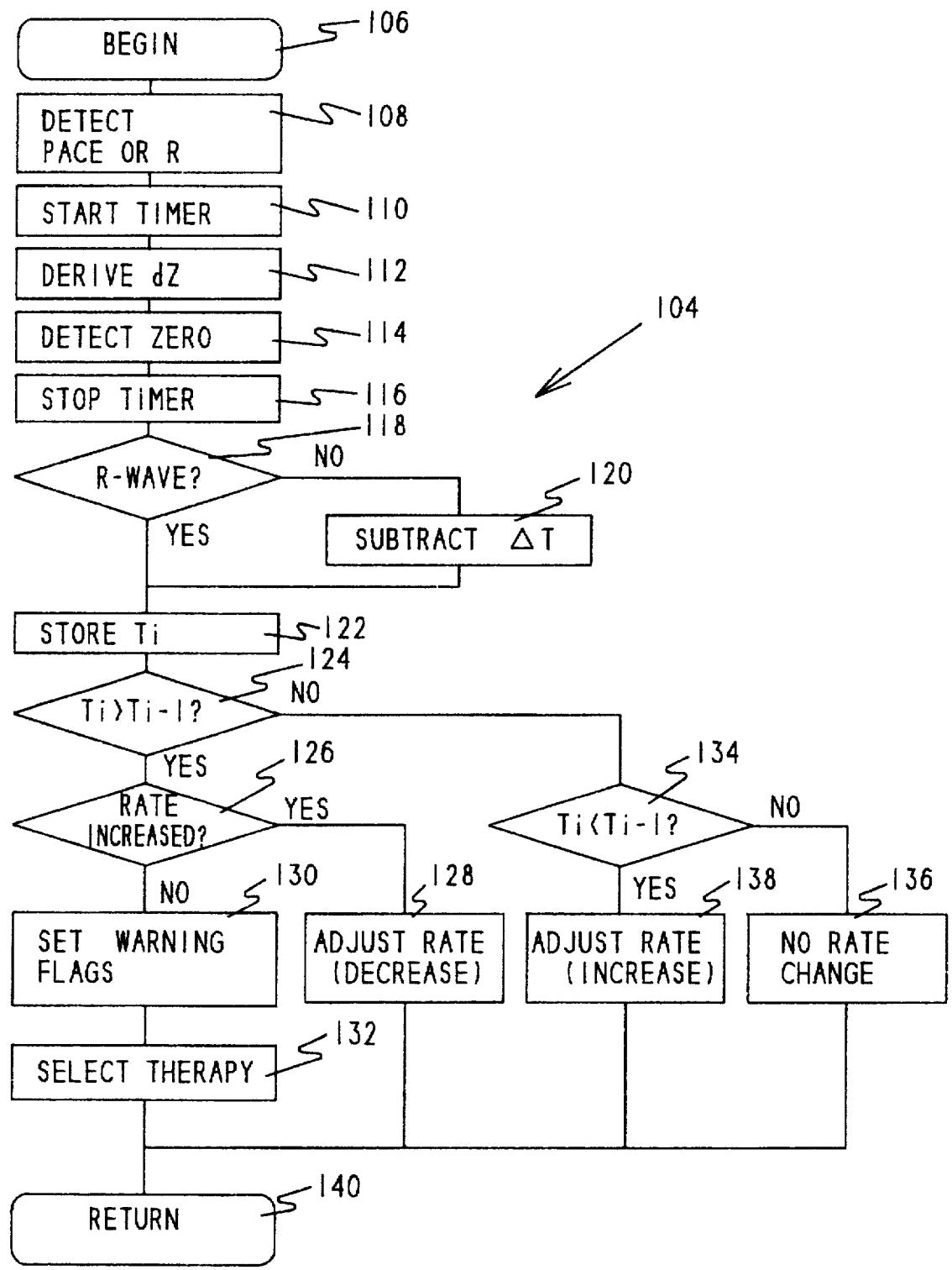
FIG. 8 is a flow chart.

The application of these principles is illustrated in FIG. 8, which shows a flow-chart for a portion 104 of the control program for use in the cardiac stimulator. Other portions of a controlled program are known in the art and are not further described here. This program segment 104 would begin 106 as part of other programming in the implantable cardiac stimulator. The cardiac stimulator would detect 108 either a pace or the occurrence of a natural R-wave, which would ordinarily inhibit the application of a pace pulse. This detection would initiate a timer 110. Information from the impedance sensor would be provided to the microprocessor of the pacer which would calculate the derivative of the impedance 112. Alternatively, a differentiating circuit could perform this function in an analog fashion. The impedance waveform itself could also be used, but, as explained above, this may be less precise. The pacemaker would then detect 114 the zero crossing 94 indicative of the maximum impedance. This would then stop the timer 116, measuring the R-Z interval. The microprocessor would then check if the R-wave was detected 118 or if the interval was commenced by a pace. If the R-wave was not detected, a period ΔT would be subtracted from the measured time interval to adjust for the approximated actual occurrence of the R-wave. The interval ΔT could be either preselected, or calculated from the current heart rate or from past cardiac cycles to derive an exemplary value for ΔT. The original or adjusted measured interval would then be stored 122 as $T_i$. This value $T_i$, representing the current R-Z interval, would then be compared 124 with a historic R-Z interval here called $T_i$-1. Interval $T_i$-1 may be derived in any number of ways. It could represent the immediate previous R-Z interval, or it may be a rolling average of R-Z intervals. In addition, different historic R-Z intervals might be used to detect acute changes in the R-Z intervals as compared to chronic changes in the R-Z interval.

If the R-Z interval is lengthening, the microprocessor would inquire if the rate had previously been increased 126. If the rate had been increased this is indicative that an adjustment has been made for increased hemodynamic demand and the heart rate could be adjusted 128, for example, decreased slightly. If the rate had not been increased, this is an indication that a chronic change in the R-Z interval is taking place and the warning flags 130 should be set to indicate an increased likelihood of life threatening ventricular arrhythmias. The microprocessor would then select 132 more aggressive therapies from a set of therapies, such as those described in Haluska et al. U.S. Pat. No. 5,002,052.

On the other hand, if the R-Z interval has not increased at step 124, the microprocessor would test 134 to see if the R-Z interval had decreased. If there has been no decrease, then no change of rate would be indicated 136. It should be understood that in each of the tests 124 and 134, it may be required that the R-Z interval increase or decrease by a preselected amount before a change is indicated, thereby providing a range within which no change of rate would be indicated at step 136. On the other hand, if the R-Z interval has decreased acutely at 134, this is an indication that may be associated with an advent of exercise and the rate of pacing adjusted 138 accordingly. The microprocessor then returns 140 to other processing.

Having identified impedance information associated with cardiac contractions, this information can then be used to control the pacing rate or other pacing parameters, such as A-V delay intervals. By controlling the pacing rate in such a manner as to keep the stroke volume, pre-ejection interval, or ejection fraction relatively constant from cycle to cycle, a physiologically appropriate pacing rate is selected.

Our invention may be embodied in other specific forms without departing from the spirit or essential characteristics thereof. The foregoing description is, therefore, to be viewed in all respects as illustrative and not restrictive. The scope of our invention is defined by the appended claims.

We claim as our invention:

1. An implantable cardiac stimulation apparatus comprising
    a hermetically sealed container, said container having therein a battery, and
    control circuitry powered by said battery, said control circuitry comprising means for producing an output to stimulate a patient's heart; means for measuring impedance within the patient's body and producing a first signal correlated to said impedance; means for producing a first derivative of said first signal; means for detecting a zero-crossing of said first derivative; means for timing an interval from said output to said zero-crossing; and means for controlling said means for producing said output as a function of said interval.

2. The implantable cardiac stimulator according to claim 1 further comprising means for detecting an intrinsic cardiac contraction and wherein said timing means comprises means for timing said interval from either said output or said intrinsic cardiac contraction.

3. The implantable cardiac stimulator according to claim 2 further comprising means for detecting a chronic change of said interval and wherein said means for controlling said means for producing said output controls said output producing means by increasing a cardiac stimulation rate after a chronic decrease of said interval has been detected and by decreasing said cardiac stimulation rate after a chronic increase of said interval has been detected, provided said cardiac stimulation rate has been increased previous thereto.

4. The implantable cardiac stimulator according to claim 2 further comprising a sensor for detecting a condition correlated to physiologic need and producing a second signal correlated to said condition, and wherein said means for controlling further controls said output producing means as a function of said second signal.

5. The implantable cardiac stimulator according to claim 1 wherein said means for controlling controls a pacing rate.

6. The implantable cardiac stimulator according to claim 1 wherein said means for controlling controls a maximum pacing rate.

7. The implantable cardiac stimulator according to claim 1 further comprising means for detecting a chronic change of said interval and wherein said means for controlling said means for producing said output controls said output producing means by increasing a cardiac stimulation rate after a chronic decrease of said interval has been detected and by decreasing said cardiac stimulation rate after a chronic increase of said interval has been detected, provided said cardiac stimulation rate had been increased previous thereto.

8. The implantable cardiac stimulator according to claim 1 further comprising a sensor for detecting a condition correlated to physiologic need and producing a second signal correlated to said condition, and wherein said means for controlling further controls said output producing means as a function of said second signal.

9. A method for controlling an implantable cardiac stimulation apparatus comprising producing a cardiac stimulating output;

measuring impedance within the patient's body;

producing a first derivative of said measured impedance;

detecting a zero-crossing of said first derivative;

timing an interval from said output to said zero-crossing; and producing a subsequent cardiac stimulating output as a function of said interval.

10. The method according to claim 9 further comprising detecting an intrinsic cardiac contraction and timing said interval from either said output or said intrinsic cardiac contraction.

11. The method according to claim 10 further comprising detecting a chronic change of said interval and controlling said output by increasing a cardiac stimulation rate after a chronic decrease of said interval has been detected and decreasing said cardiac stimulation rate after a chronic increase of said interval has been detected, provided said cardiac stimulation rate had been increased previous thereto.

12. The method according to claim 10 further comprising detecting a condition correlated to physiologic need, and controlling said output as a function of said detected condition.

13. The method according to claim 9 where in said step of controlling comprises controlling a pa cing rate.

14. The method according to claim 9 wherein said step of controlling comprises controlling a maximum pacing rate.

15. The method according to claim 9 further comprising detecting a chronic change of said interval and controlling said output by increasing a cardiac stimulation rate after a chronic decrease of said interval has been detected and decreasing said cardiac stimulation rate after a chronic increase of said interval has been detected, provided said cardiac stimulation rate had been increased previous thereto.

16. The method according to claim 9 further comprising detecting a condition correlated to physiologic need, and controlling said output as a function of said detected condition.

* * * * *